United States Patent
Metcalf et al.

[19]

[11] Patent Number: 5,864,396
[45] Date of Patent: Jan. 26, 1999

[54] COLOR COMPARATOR SYSTEM

[75] Inventors: Raymond W. Metcalf, Milliken; Annette R. Geiselman; Arthur E. King, both of Ft. Collins, all of Colo.

[73] Assignee: Hach Company, Loveland, Colo.

[21] Appl. No.: 84,684

[22] Filed: May 26, 1998

[51] Int. Cl.⁶ ..................................................... G01J 1/02
[52] U.S. Cl. ........................ 356/243; 356/402; 356/407; 356/408
[58] Field of Search .................................. 356/243, 402, 356/408, 407

[56] References Cited

U.S. PATENT DOCUMENTS

| | | | |
|---|---|---|---|
| 3,977,789 | 8/1976 | Hunter et al. | 356/243.1 |
| 4,636,073 | 1/1987 | Williams | 356/243.1 |
| 5,204,733 | 4/1993 | Deshayes | 356/243.1 |

*Primary Examiner*—Robert Kim
*Assistant Examiner*—Reginald A. Ratliff
*Attorney, Agent, or Firm*—Dean P. Edmundson

[57] ABSTRACT

A color comparator system is described which avoids the use of liquid reference standards and glass vials. In a preferred embodiment the system includes (a) a clear lens piece including a plurality of lens sections equal to the desired number of color steps or intensities to be measured or observed; (b) background color for visually separating the lens sections and providing a controlled background color for samples between lens sections; and (c) at least one lens color means positioned behind the lens piece. The visual perception when using this comparator system is the same as viewing a series of glass tubes filled with colored liquid. Ambient light passes through each lens and is then reflected back toward the viewer.

8 Claims, 4 Drawing Sheets

COLOR COMPARATOR SYSTEM

FIELD OF THE INVENTION

This invention relates to systems and techniques utilizing visual detection color standards in visual chemical determinations.

BACKGROUND OF THE INVENTION

Chemical test kits which utilize various calorimetric methods for the determination of any of several different chemical species have long been used. In calorimetric testing, the concentration of a particular chemical substance is determined by measuring the color intensity of the sample. In some cases the color in the sample is due to the species of interest while in most cases one or more chemicals are added to the sample to react with the species of interest so as to develop a color whose intensity is in proportion to the concentration of the species being determined. In some rare cases, color is bleached from samples in proportion to an analyte concentration.

Mathematically, the amount of light passing through a colored material is inversely proportional to the concentration of the colored species and the path length of the light passing through the material When using similar sample cells, the light passing through a sample is inversely proportional to the analyte concentration. In other words, the color of the sample is proportional to the analyte concentration, except for bleaching reactions.

Visual detection of color intensity is limited by several physiological factors. The human eye's color perception is not directly proportional to light intensity and color perception varies considerably between individuals. Even for one person, several factors limit the color perception. Instruments can use a narrow band of light wavelength and quantify the light intensity consistently. The human eye detects all wavelengths simultaneously and perceives a combined signal. Besides the inherent difficulties in basic color perception, differences in shape of objects, gloss, texture, light source and background variations also complicate color differentiation comparison of similar colors.

Several methods have been used to provide reference colors or standards for visual comparison of between unknown samples and references for calorimetric determinations. One of the most common has been to provide colored liquids in sealed glass tubes similar to the tubes used for samples. This method has the advantage of being the most visually similar to samples, but is relatively complicated and expensive to prepare, and the tubes of standards are fragile. If the tubes are dropped, they may break and the color reference is lost, making testing impossible. Complications in production include: (1) actual test chemistry may not produce a suitably stable color, and (2) other materials used to provide the color must provide similar color perception for both hue and intensity in a wide variety of ambient light conditions (dyes commonly have different absorption spectrums than found in chemical tests and may be perceived correctly using the one light source and be obviously different with another light source), and (3) some desirable color dyes and solutions are hazardous.

Other methods of providing reference colors have included: (1) colors printed on a variety of materials, (2) colored transparent glass or plastic pieces, and more recently, (3) color pieces of varying depth which provide the perception of different intensities of the same hue all from one material (e.g., Hach color cubes and color discs). This approach eliminated much of the expense in preparing the reference colors and the fragility problem, but increased difficulties due to change in shape, texture, gloss and backgrounds.

There has not heretofore been provided a color comparator having the features and advantages provided by the present invention.

SUMMARY OF THE PRESENT INVENTION

It is one object of the present invention to provide a color comparator system for visual testing in which all color reference standards may be perceived as being similar in shape, texture and gloss as the test samples.

It is another object of the invention to provide a system which avoids the use of liquid reference standards and glass vials.

It is yet another object of the invention to provide colored reference standards which are stable and do not vary with aging.

It is yet another object of this invention to provide a system in which the standard reference colors are perceived as the correct hue regardless of ambient light source.

It is still another object of the invention to provide a color comparator system which includes a wide range of color intensity to cover reasonable concentration ranges being tested.

It is another object of the invention to provide a system in which the color reference material is composed of one material of varying thickness.

These and other objects are achieved by the color comparator system of this invention which may comprise:

(a) a clear lens piece including a plurality of lens sections equal to the desired number of color steps or intensities to be measured or observed;

(b) background color means for visually separating the lens sections and providing a controlled background color for samples between lens sections; and (c) at least one lens color means positioned behind the lens piece.

The comparator system of the invention is very easy to use and provides reliable results without the need for colored liquid reference standards or glass tubes. The visual perception when using this novel comparator system, however, is the same as viewing a series of glass tubes filled with colored liquid. Ambient light passes through each lens and is then reflected back toward the viewer. The perception of varying color intensity is obtained by varying the thickness of transparent colored pieces between the lens piece and a reflective light-colored opaque backing. This creates the desired illusion of varying concentration of colored liquids.

The desired image of a glass tube with colored liquid is simulated adequately to permit good color perception accuracy while being less expensive than previously available systems. The comparator system is also useful in two color chemistries by use of two colored pieces behind the lens piece.

Other advantages and features of the comparator system of the invention will be apparent from the following detailed description and accompanying drawings.

BRIEF DESCRIPTION OF THE DRAWINGS

The invention is described in more detail hereinafter with reference to the accompanying drawings, wherein like reference characters refer to the same parts throughout the several views and in which.

DETAILED DESCRIPTION OF THE INVENTION

Figure 1:
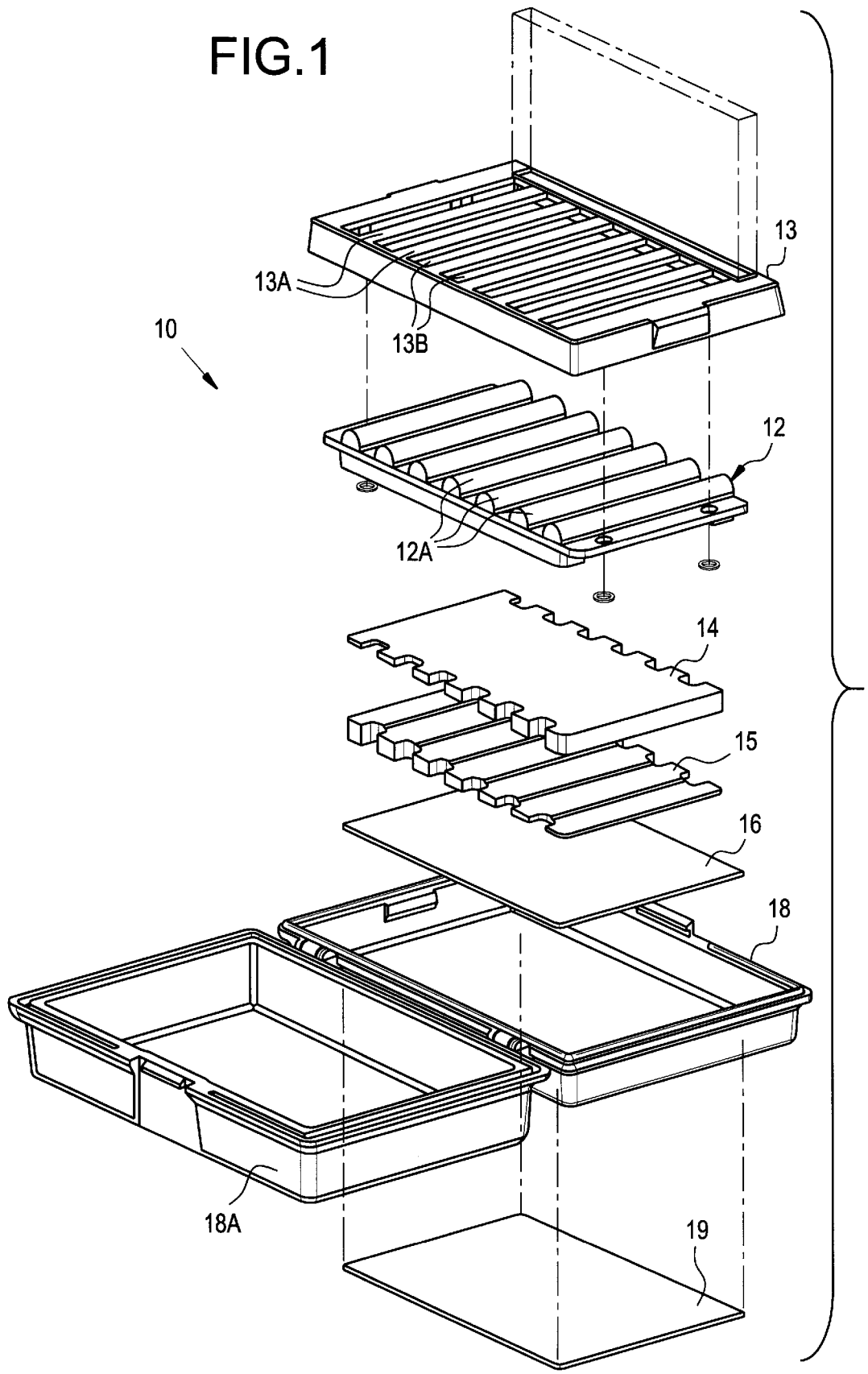
FIG. 1 is an explosion view of a preferred embodiment of color comparator system of the invention.
Figure 2:
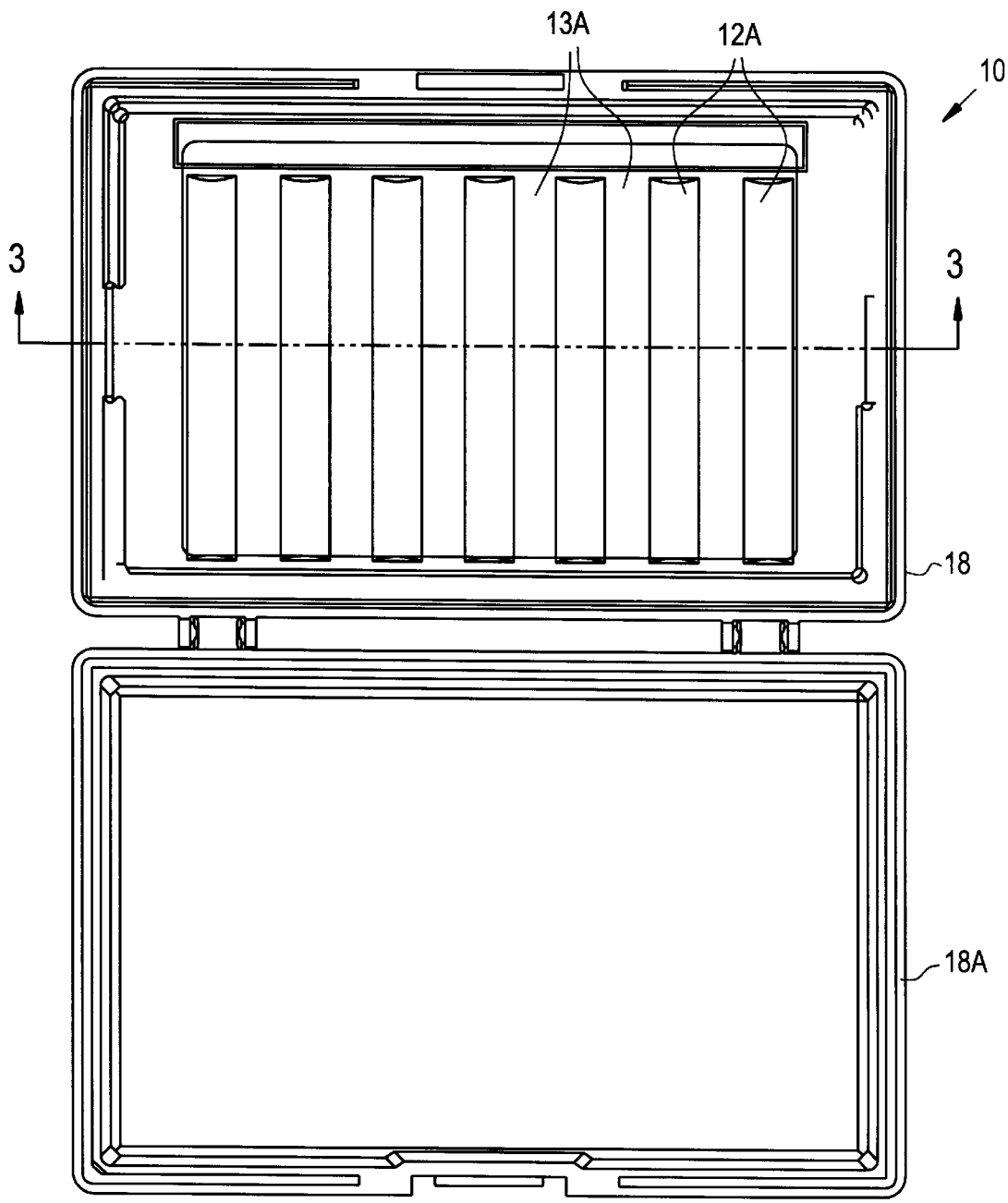
FIG. 2 is a top view of the embodiment of color comparator shown in FIG. 1.
Figure 3:
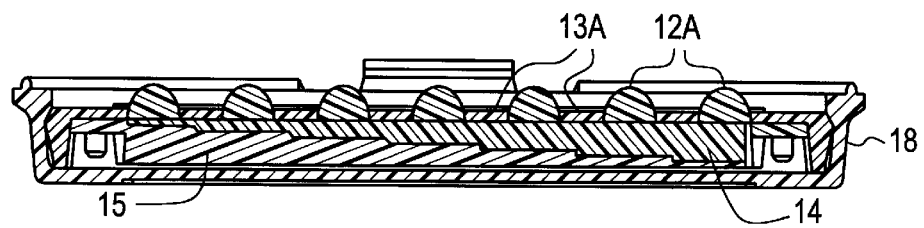
FIG. 3 is a cross-sectional view of the color comparator taken along line 3—3.
Figure 4:
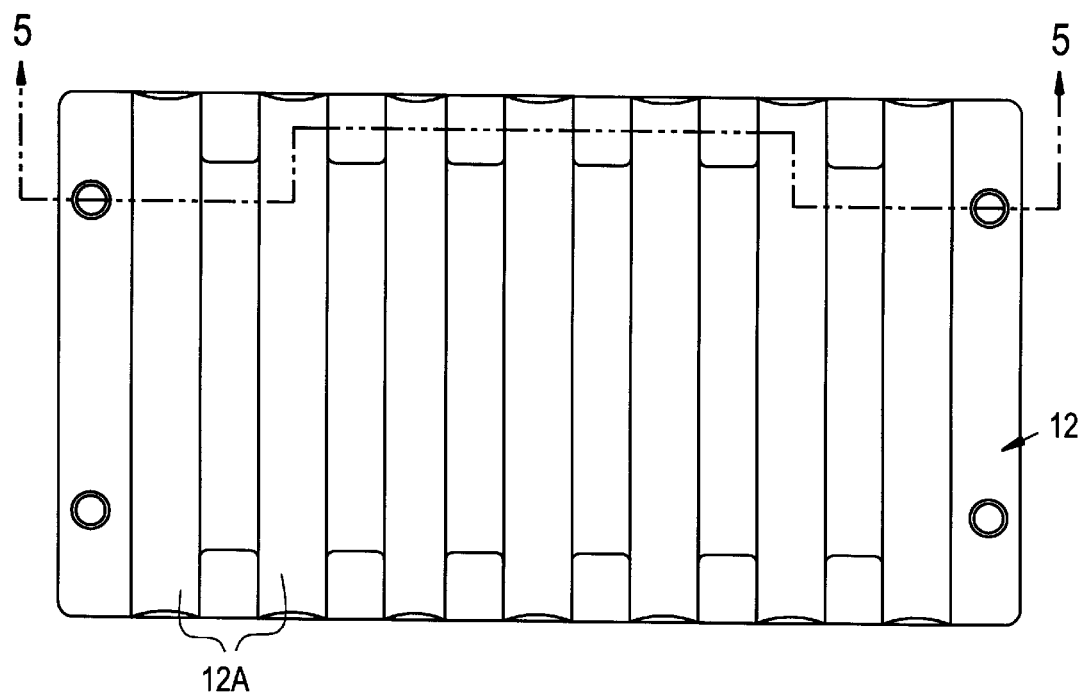
FIG. 4 is a top view of a preferred lens piece for use in this invention.
Figure 5:
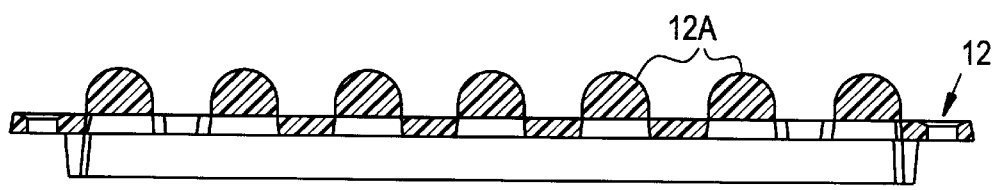
FIG. 5 is a cross-sectional view taken along line 5—5 in FIG. 4.
Figure 6:
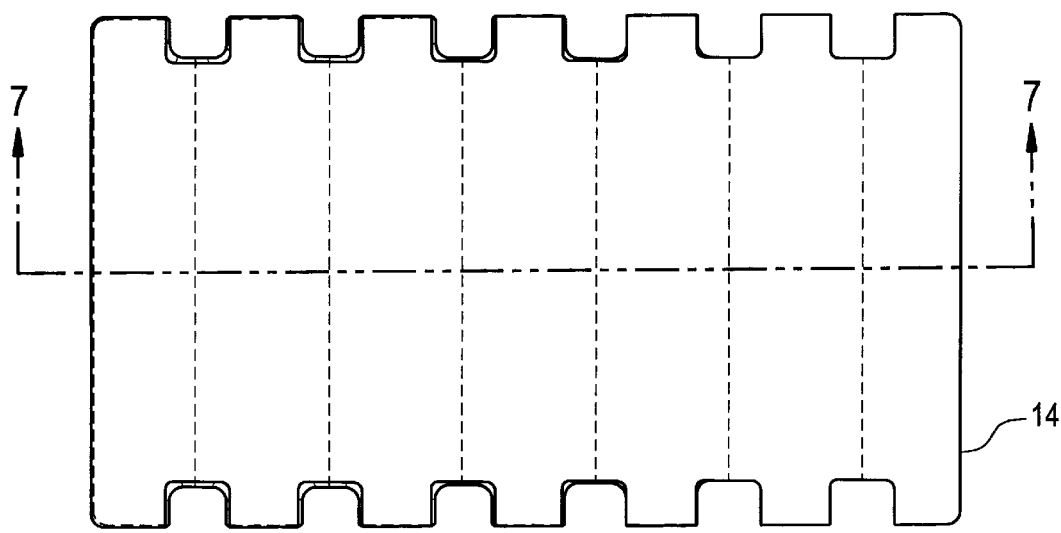
FIG. 6 is a top view of a preferred color chip means for use in this invention.
Figure 7:
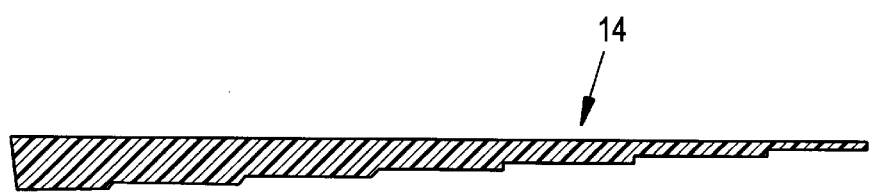
FIG. 7 is a cross-sectional view taken along line 7—7 in FIG. 6.

In the drawings there is shown a preferred embodiment of a color comparator system of this invention. The system 10 comprises a lens piece 12, color chips 14 and 15, opaque backing sheet or element 16, box 18, and body 13. The body 13 includes alternating openings or slots 13 B and solid sections 13A which are parallel to each other, as shown. The slots 13B receive the lens sections 12A which are in the form of elongated, spaced-apart clear plano-convex lens sections. Preferably, the lens sections are integrally connected, in the manner shown in the drawings.

The color of the body 13 is selected to optimize the color between lens sections 12A so that the background behind sample vials which are held in front of the body 13 enables optimal color matching of the sample vials with the colors viewed through the lens sections. The lens piece 12 is preferably composed of clear plastic with a gloss matching that of glass.

The color chip 14 includes a number of steps or graduated thicknesses, as shown. The color intensity in the thicker steps or gradations is greater than in the thinner steps. A separate step or gradation is located behind each separate lens section 12A.

For single color chemistries the colored chip 14 is placed next to and directly behind the lens piece and the second chip 15 is clear and colorless. For two color chemistries, the second chip 15 exhibits the second desired color. The dye colors and intensities are selected for matching samples and for stability.

Color chip backing member 16 reflects light entering the lens sections back through the color chips 14 and 15 and out through the lens. Member 16 must be reflective and opaque (and it preferably is white in color). Its color may vary to enhance color perception in some circumstances such as adding a uniform color to all color chip sets. When the color comparator system is enclosed in a suitable case, the color chip backing member 16 may be omitted if the surface behind the comparator meets the requirements of the color chip backing.

The box 18 is a convenient carrying case for the color comparator kit. It includes a hinged lid 18A. An appropriate label 19 may be adhered to the case, if desired.

There may be any desired number of lens sections 12A in the lens piece. Appropriately there would be a corresponding number of steps or gradations in the color chips 14 and 15.

The color comparator system of the invention is used by placing test samples (having unknown concentrations of a particular chemical species) beside the various lens sections and comparing the sample color with the color seen in the lens. The analyte concentration for the step corresponding to the closest color match, or a value which is interpolated between two adjacent steps, is recorded as the test sample's concentration of the particular chemical species of concern.

Other variants are possible without departing from the scope of this invention.

What is claimed is:

1. A color comparator system for visually comparing the color of a test solution with a series of color standards, the system comprising:

(a) a plurality of lens sections;

(b) background color means for visually separating the lens sections and providing a controlled background color between said lens sections for a test sample; and (c) at least one lens color means positioned behind said lens sections; wherein said color means provides a color of different intensity behind each said lens section.

2. A system in accordance with claim 1, wherein each said lens section comprises a plano-convex lens.

3. A system in accordance with claim 1, wherein said lens sections are parallel to each other.

4. A system in accordance with claim 2, wherein said lens sections are integrally connected.

5. A system in accordance with claim 1, wherein said lens color means comprises a colored plastic chip having first and second ends, and wherein the thickness of said chip increases from said first end to said second end.

6. A system in accordance with claim 5, wherein said chip includes a plurality of steps with progressively greater thickness from one said step to an adjacent step.

7. A system in accordance with claim 6, wherein the number of said steps is equal to the number of said lens sections.

8. A system in accordance with claim 1, further comprising a housing with an openable lid for containing said system.

* * * * *